United States Patent
Thompson

(10) Patent No.: US 7,559,227 B2
(45) Date of Patent: Jul. 14, 2009

(54) PNEUMATIC TESTING FOR GAS CHROMATOGRAPH INLET

(75) Inventor: Michael Q. Thompson, Coatesville, PA (US)

(73) Assignee: Agilent Technologies, Inc., Santa Clara, CA (US)

(*) Notice: Subject to any disclaimer, the term of this patent is extended or adjusted under 35 U.S.C. 154(b) by 83 days.

(21) Appl. No.: 11/611,771

(22) Filed: Dec. 15, 2006

(65) Prior Publication Data

US 2008/0141758 A1    Jun. 19, 2008

(51) Int. Cl.
*G01N 30/04* (2006.01)
*B01D 53/02* (2006.01)

(52) U.S. Cl. .................. 73/23.42; 73/23.35; 95/22; 95/23; 95/82

(58) Field of Classification Search ............... 73/23.35, 73/23.42; 95/12, 15, 19, 22, 23, 82
See application file for complete search history.

(56) References Cited

U.S. PATENT DOCUMENTS

| 5,670,707 | A | * | 9/1997 | Fennell et al. | ............. 73/19.02 |
| 5,938,817 | A | | 8/1999 | Shibamoto et al. | |
| 6,338,823 | B1 | * | 1/2002 | Furukawa | .................. 422/89 |

FOREIGN PATENT DOCUMENTS

| JP | 4-93654 A | * | 3/1992 | ............... 73/23.35 |
| JP | 5-45350 A | * | 2/1993 | ............... 73/23.35 |
| JP | 2000-275230 A | * | 10/2000 | |

* cited by examiner

*Primary Examiner*—Daniel S Larkin

(57) ABSTRACT

A method and apparatus for detecting a flow disruption within a gas chromatograph (GC) inlet. A controller controls an input flow of a gas entering a chamber of the GC inlet, and the output flow of gas leaving the chamber. A flow disruption is detected when at least one of the input and output flows deviates from a target value.

18 Claims, 7 Drawing Sheets

US 7,559,227 B2

PNEUMATIC TESTING FOR GAS CHROMATOGRAPH INLET

BACKGROUND OF THE INVENTION

A gas chromatograph (GC) is an instrument that is used to separate volatile components of a sample. A GC is typically used in combination with a suitable detector (e.g. a mass spectrometer) to analyze, identify, and/or measure individual components within the sample.

FIG. 1 shows a high-level schematic diagram of a portion of an exemplary gas chromatograph (GC) 10. The GC 10 includes a GC inlet 11 connected to a column 20. A carrier gas 18 flows into an inlet body 12 via an input path 22. A liquid sample 15 is introduced into the inlet body 12 by a needle 14. The inlet body 12 is a heated chamber for evaporating the liquid sample 15. The inlet body 12 is covered by a septum 16, which is a flexible material through which the needle 14 is inserted to inject the liquid sample 15. A portion of the carrier gas 18 flows underneath the septum 16 to prevent contamination of the current analysis by material left on the septum by previous injections. This flow exits through the septum purge 17. The components of the sample 15 separate within a column 20 based on their physical characteristics and are carried by the carrier gas 18 to a detector (not shown).

The septum 16 is made of a flexible material (such as rubber) which is capable of being pierced by the needle 14. The flexible material also conforms around the needle 14 to create a seal, so that the contents of the inlet body 12 do not escape through any gaps between the septum 16 and the needle 14. Once the needle 14 is removed, the flexible material of the septum 16 rejoins and closes up the hole that was created by the needle 14 when it pierced the septum 16. Some septa have pre-formed holes for inserting the needle.

However, the septum 16 is prone to developing leaks because its ability to reseal the holes formed by the needle degrades over time and repeated use. Any leakage from the septum 16 is problematic because it may invalidate a GC measurement.

Various methods have been used in the past to try to prevent or manage septum leaks. For example, some users schedule a change of the septum on a regular basis, e.g. once a week. However, septum leaks are random so a replacement schedule only gives a margin of protection.

Furthermore, changing the septum alone will not prevent or cure leaks elsewhere within the GC inlet 11. For example, another possible source of leaks is around a column ferrule, which connects the column 20 to the inlet body 12. Such a leak could be the result of temperature cycling or may happen during column maintenance. A leak may even be caused by a broken column. Other flow disruptions that invalidate a GC measurement—such as clogs or other obstructions—may also exist.

Therefore, there remains a need for an improved method and apparatus for detecting leaks and other flow disruptions within the GC.

DETAILED DESCRIPTION

Figure 1:
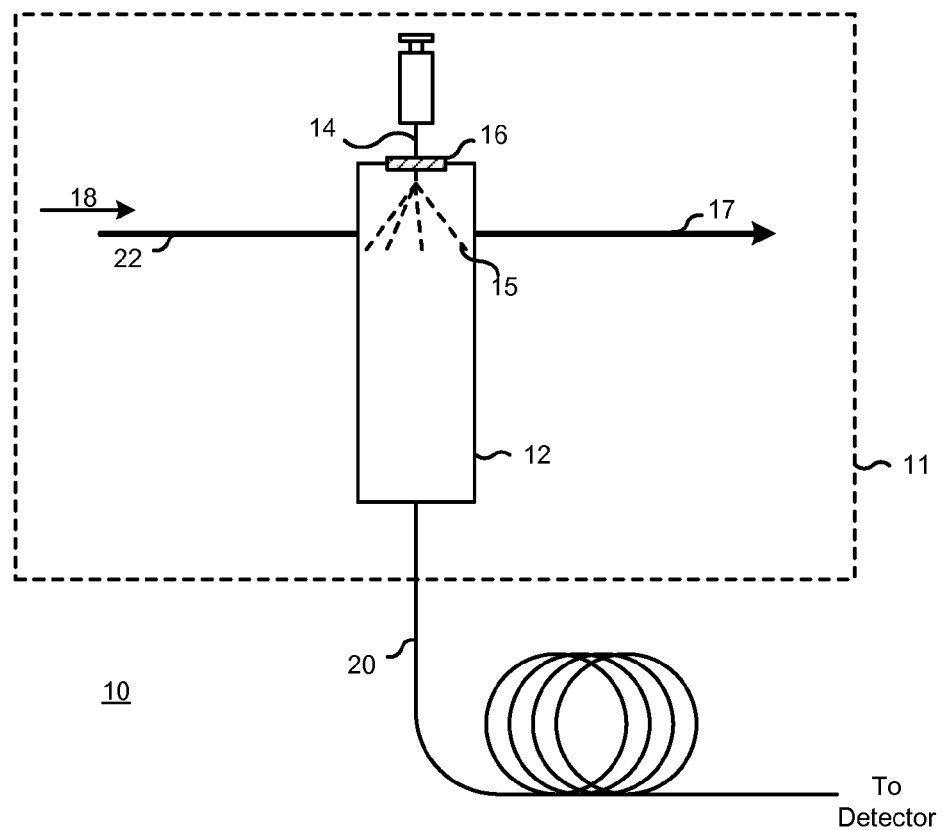
FIG. 1 shows a high-level schematic diagram of a portion of an exemplary gas chromatograph (GC).
Figure 2:
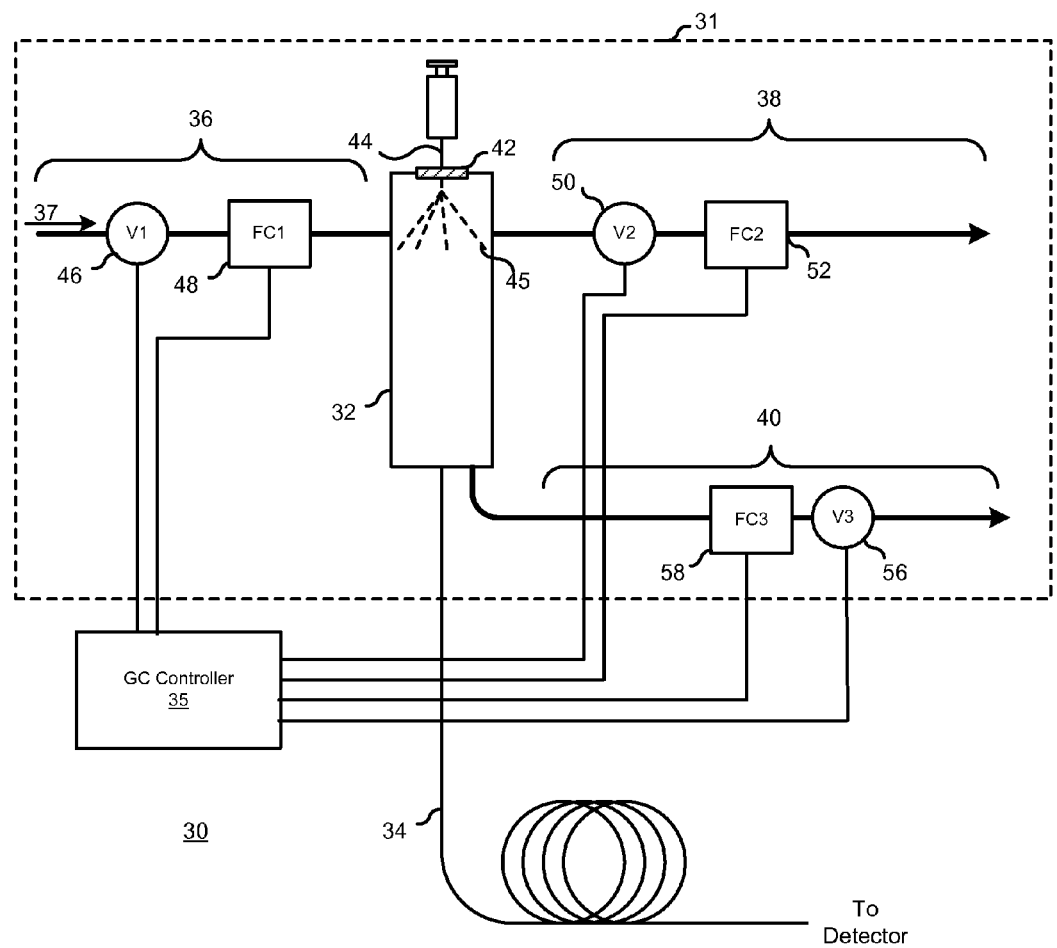
FIG. 2 shows a schematic diagram of a portion of a GC.

FIG. 2 shows a schematic diagram of a portion of a gas chromatograph (GC) 30. The GC 30 includes a GC inlet 31 that leads to a column 34, and a GC controller 35 for controlling the GC 30. The GC 30 includes other components that are not shown here, to avoid unnecessarily complicating the figure and the discussion below.

The GC inlet 31 includes an inlet body 32, an input branch 36 for bringing carrier gas 37 into the inlet body 32, a septum purge branch 38 for exhausting carrier gas 37 from the inlet body 32, and a split vent branch 40 which also exhausts carrier gas 37 from the inlet body 32.

The inlet body 32 is covered by a septum 42. A needle 44 is inserted through the septum 42 to inject a sample 45 into the inlet body 32. The inlet body 32 vaporizes the sample 45, which is then carried by the carrier gas 37 through the column 34 to a detector (not shown). A portion of the carrier gas 37 flows underneath the septum 42 and out of the inlet body 32 through the septum purge branch 38 to keep the underside of the septum 42 free from sample contamination. The remainder of the carrier gas 37 is divided between the column 34 and the split vent branch 40. The split vent branch 40 regulates the amount of sample 45 that is carried into the column 34 and provides an exit path for excess sample 45.

The input branch 36 includes a valve 46 ("V1") and a flow calculator 48 ("FC1"). The septum purge branch 38 includes a valve 50 ("V2") and a flow calculator 52 ("FC2"). The split vent branch 40 includes a valve 56 ("V3") and a flow calculator 58 ("FC3"). Valve V1 regulates the flow of carrier gas 37 entering the inlet body 32 through the input branch 36. Valve V2 regulates the flow of carrier gas 37 exiting the inlet body 32 through the septum purge branch 38. Valve V3 regulates the flow of carrier gas 37 exiting the inlet body through the split vent branch 40. Valves V1, V2, and V3 are all electronically controlled by the GC controller 35 and can be varied between completely closed and completely opened positions.

The flow calculators FC1, FC2, and FC3 are mechanisms or devices that are capable of determining the flow of carrier gas through the respective branch in which the flow calculator is located. For example, a flow sensor such as a Honeywell Mass Airflow Sensor, AWM40000 series, part number AWM42150VH can be used to implement a flow calculator. The flow calculators FC1, FC2, and FC3 are electronically controlled by and in electronic communication with the GC controller 35 as well. Flow is normally measured in milliliters per minute, referenced to a pressure of 1.0 atmosphere and a temperature of 298.15 degrees Kelvin.

When no leaks are present in the septum 42 or elsewhere within the GC inlet 31, the total flow of carrier gas 37 into the inlet body 32 should equal the sum of all the flows of carrier gas out of the inlet body. In other words, in the absence of a leaky septum or other unmeasured flow, the flow of carrier gas into the inlet body 32 through input branch 36 should be equal to the flows of gas out of the inlet body through the known output paths: the column 34, the septum purge branch 38, and the split vent branch 40. This situation can be represented by the following equations:

$$\text{flow}_{input} = \text{flow}_{output} \tag{1}$$

$$\text{flow}_{input} = \text{flow}_{column} + \text{flow}_{septum\_purge} + \text{flow}_{split\_vent} \tag{2}$$

where $\text{flow}_{input}$ is the flow of carrier gas 37 into the GC inlet 31, $\text{flow}_{column}$ is the flow of carrier gas through the column 34, $flow_{septum\_purge}$ is the flow of carrier gas through the septum purge branch 38, and $flow_{split\_vent}$ is the flow of carrier gas through the split vent branch 40. It should be noted that variations to the GC inlet 31 shown in FIG. 2 can be made without departing from the teachings of the present invention. For example, some GC inlets lack a septum purge branch 38, while others lack a split vent branch 40. Equations 1 and 2 would still apply to such GC inlets, but output flows would need be calculated only for existing output paths in a particular GC inlet configuration.

A difference between $flow_{input}$ and $flow_{output}$ should exceed a certain error threshold for a leak to be inferred from an imbalance in equation (2). Slight differences between $flow_{input}$ and $flow_{output}$ that are beneath that error threshold can be attributed to imperfect or non-ideal components that perform the calculations. The error threshold may be adjusted to tune the sensitivity of the leak detection to the preference of the user. These calculations are performed by the GC controller 35. The GC controller 35 is implemented with a microprocessor or other programmable device that can electronically control and communicate with the valves and flow calculators within the GC inlet 31.

To determine whether there is a leak in the GC inlet 31, the GC controller 35 needs to determine $flow_{input}$, $flow_{column}$, $flow_{septum\_purge}$, and $flow_{split\_vent}$. $Flow_{input}$ is measured by FC1, $flow_{septum\_purge}$ is measured by FC2, and $flow_{split\_vent}$ is measured by FC3. These values are reported back to the GC controller 35. The calculation for $flow_{column}$ is performed by the GC controller 35 based on known quantities including the dimensions of column 34, the type of carrier gas 37 used, and the temperature of the column 34. This calculation is well-known by one of ordinary skill of the art and is typically readily available as a value reported by most gas chromatographs. Therefore, it will not be discussed here in further detail. Instead, the reader is referred to the following reference for more information on how to calculate $flow_{column}$ :"Electronic Pressure Control in Gas Chromatography", edited by Sally S. Stafford, Hewlett-Packard Company, 1993, part number 5182-0842.

Next, the GC controller 35 inserts these values into equation (2). If $flow_{output}$ adds up to less than $flow_{input}$, then there is a leak in the GC inlet 31. The likely source of that leak will differ, depending on the circumstances in which the leak is discovered. For example, if the leak is detected after a part has been repaired or replaced, the source of the leak is most likely that repaired/replaced part. However, if the leak is detected in between runs, the source of the leak is likely to be the septum. Also, a column may break at any time, so the column should also be checked when a leak is detected.

Once a leak has been detected, the GC controller 35 can issue an alert about the leak. Upon receipt of an alert, a GC user can choose to fix the leak part, or to proceed with the knowledge that a leak exists somewhere within the GC inlet 31.

In one embodiment, the calculation of equation (2) is made simpler by closing one or more valves that control an output path for carrier gas out of the inlet body 32 so as to set one or more flow calculations to zero. For example, the GC controller 35 can completely close V3, leaving only V1 and V2 open. Then $flow_{split-vent}=0$, and only $flow_{input}$, $flow_{column}$, and $flow_{septum-purge}$ need to be determined. In another example, the GC controller 35 can close both V2 and V3. Then $flow_{septum-purge}=flow_{split\_vent}=0$, and only $flow_{input}$ and $flow_{column}$ need to be determined.

In one embodiment, the GC controller 35 can check for flow disruptions within the column by comparing the total input flow as measured by FC1 to the flow value for the column as calculated by the GC controller 35, to determine whether the column 34 is functioning properly. The GC controller 35 closes V2 and V3, leaving only V1 open. In the absence of any leaks, the only path for carrier gas to flow out of the GC is through the column 34, so that $flow_{input}$ should equal $flow_{column}$. As mentioned before, $flow_{column}$ is a value calculated by the GC controller 35 based on known quantities including the dimensions of column 34, the type of carrier gas 37 used, and the temperature of the column 34. If the column 34 is obstructed in some way by a clog, $flow_{input}$ will be lower than $flow_{column}$. Therefore, if FC1 measures $flow_{input}$ to be lower than $flow_{column}$ as calculated by the GC controller 35, the GC controller 35 can conclude that column 34 is clogged and issue an appropriate alert. Conversely, if $flow_{input}$ is measured to be higher than $flow_{column}$, then there is a leak within the GC inlet 31.

Figure 3A:
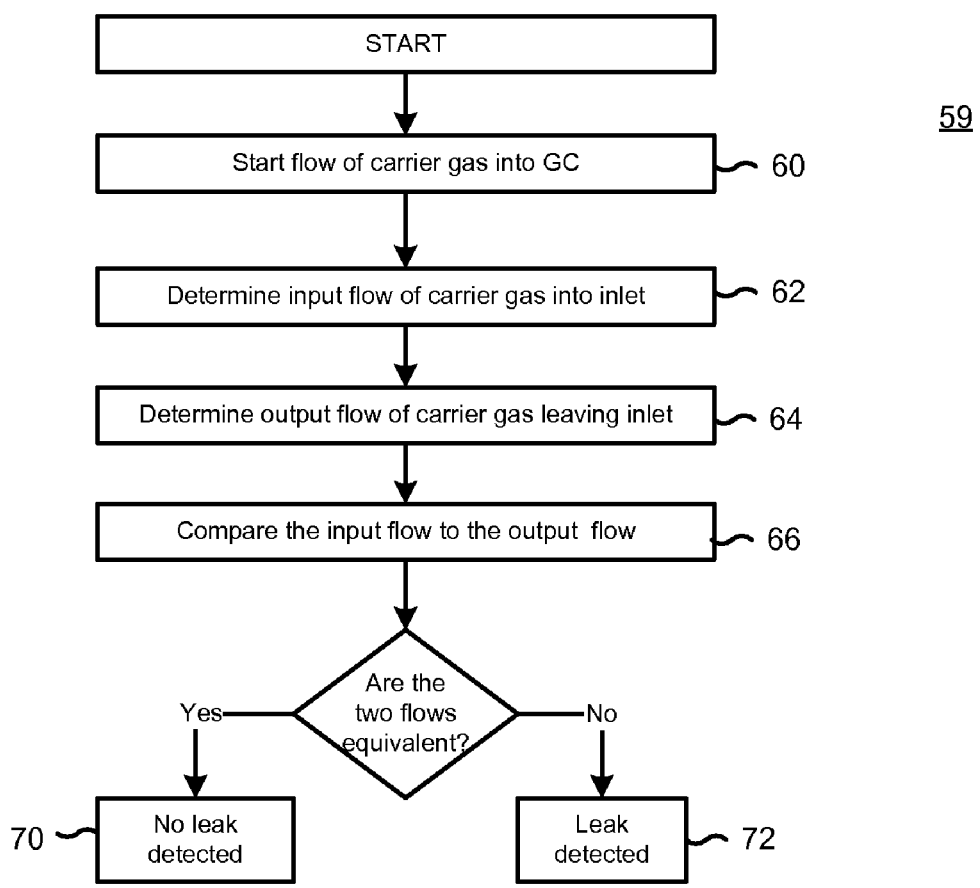
FIG. 3A is a flow chart illustrating a method.

FIG. 3A is a flow chart illustrating a method 59 according to one embodiment. First, the GC inlet 31 is set to run with a flow of carrier gas (step 60). No sample needs to be injected into inlet body 32, since this process is used only as leak detection test and not as an actual measurement. Then, the input flow of carrier gas ($flow_{input}$) into the inlet body 32 is determined (step 62). In step 64, the output flow of carrier gas ($flow_{output}$) leaving the inlet body 32 in known output paths is calculated. For example, the known output paths from the inlet body 32 in FIG. 2 are the column 32, the septum purge branch 38, and the split vent branch 40. The corresponding flow values for these output paths are $flow_{column}$, $flow_{septum\_purge}$, and $flow_{split\_vent}$, respectively. As mentioned previously, not every GC inlet has a septum purge branch or a split vent branch. Therefore, flow values only need to be calculated for the output paths that exist in a particular GC inlet.

In step 66, the input flow from step 62 is compared to the output flow from step 64. If the two flows are equivalent, then no flow disruption is detected (step 70). If there is a difference between the two flows that exceeds an error threshold, then a leak exists in the GC inlet 31 (step 72). These steps are all performed by the GC controller 35. As mentioned previously, the error threshold may be adjusted to tune the sensitivity of the leak detection to the preference of the user.

This method 59 of checking for flow disruptions can be initiated as needed by the user and run by the GC controller 35 as a routine. Or, the GC controller 35 can be programmed to run this test automatically at regular intervals (e.g. after every run, or every day, etc.) or pre-programmed intervals to maintain the GC in working condition.

Figure 3B:
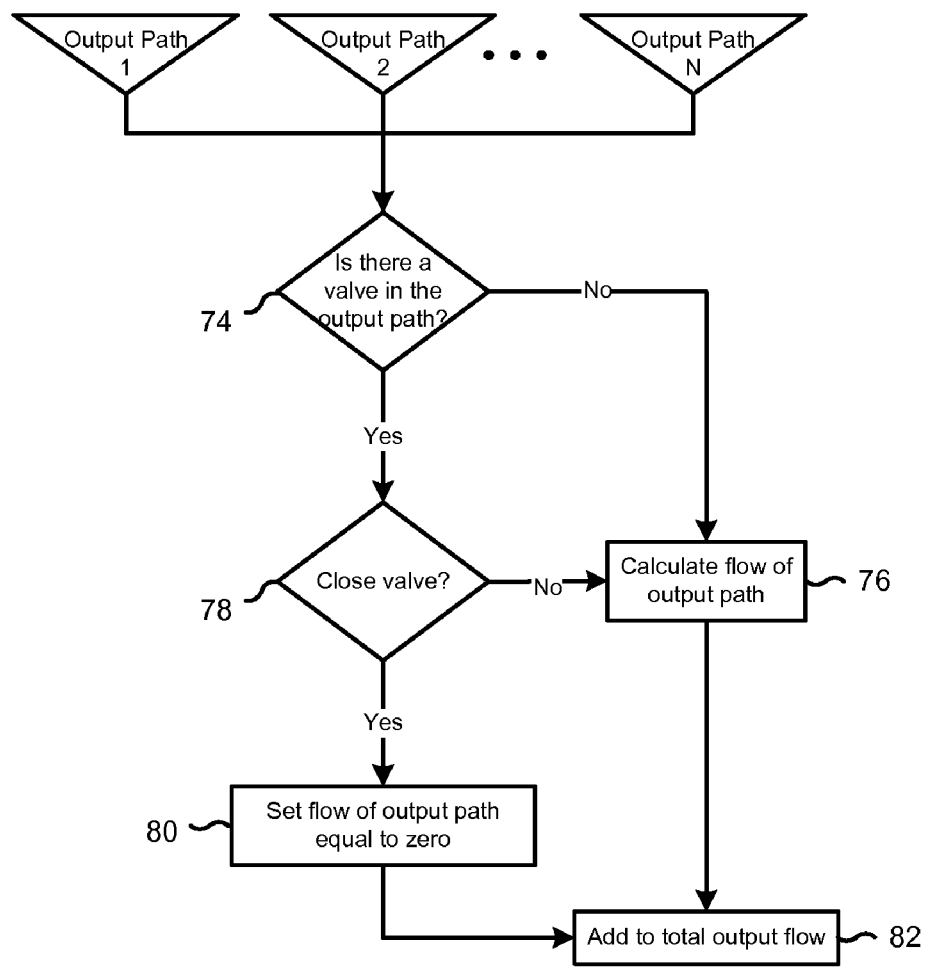
FIG. 3B is a flow chart illustrating a method.

FIG. 3B is a flow chart providing more detail on how to determine the output flow in the output paths from the GC inlet (step 64 in FIG. 3A). This method is repeated for each output path (labeled output paths 1 to N) from the GC inlet. In the case of the GC system of FIG. 2, the output paths would be the column 32, the septum purge branch 38, and the split vent branch 40. The calculation for the output flow in each path depends on whether a valve exists in the path or not (step 74). When there is no valve, then the flow of the output path should be calculated (step 76). Again returning to the example of FIG. 2, the output flow would need to be calculated for the column 32, since no valve exists in that particular output path.

When a valve exists in the path, a decision must be made by the GC controller whether to close the valve (step 78). When the valve remains open, the flow of the output path still needs to be calculated (step 76). However, if the GC controller has no way of calculating the flow through the output path (e.g. the required sensors/devices/mechanisms are not in place), then step 76 is not an option. When the valve is closed, no flow of gas is possible through the output path. The flow of the output path is equal to zero, and no calculations or measurements of the flow need to be made (step 80). Finally, the total output flow is determined by adding up the output flows determined for each path (step 82).

Figure 4:
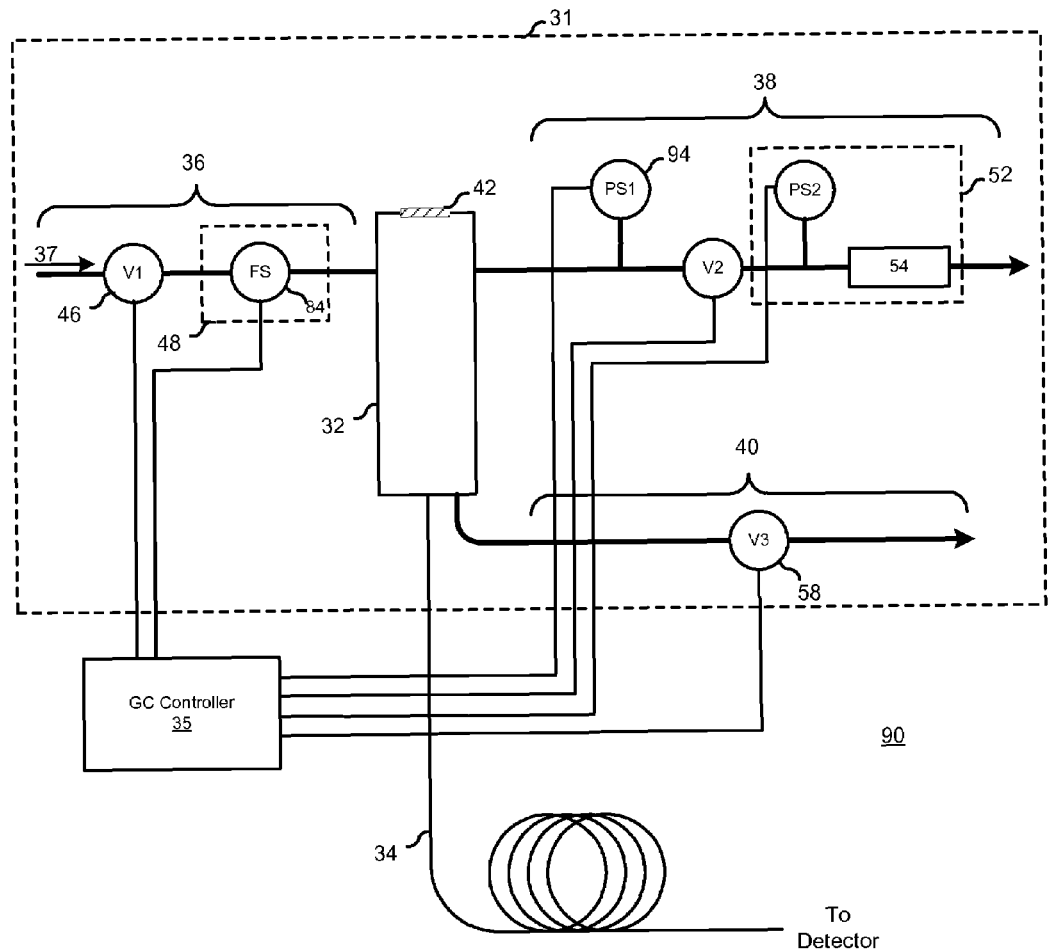
FIG. 4 illustrates a GC in an actual reduction to practice.

FIG. 4 illustrates a portion of a GC 90 in an actual reduction to practice. GC 90 includes a GC inlet 31 that leads to a column 34, and a GC controller 35 for controlling the GC 90. The function of the flow calculator 48 shown in FIG. 2 is implemented by the flow sensor 84 ("FS") such as the Honeywell Mass Airflow Sensor previously described. The flow sensor FS determines flow$_{input}$, which is the flow through the input branch 36. A pressure sensor 94 ("PS1") monitors the pressure in the inlet body 32. The pressure sensor PS1 is also in electronic communication with the GC controller 35.

The function of the flow calculator 52 shown in FIG. 2 is implemented by two devices: a second pressure sensor 96 ("PS2") and a frit 54. The pressure sensor PS2 is a gauge pressure sensor that monitors the pressure across the frit 54, and is in electronic communication with GC controller 35. The frit 54 is a calibrated restriction; the GC controller 35 is programmed with a calibration table that correlates the pressure across the frit to a flow value. The values in the table will vary depending on the type of frit 54 used. The flow through the frit can be determined by the GC controller 35 based on known quantities, including the pressure across the frit 54 as measured by pressure sensor PS2, the type of carrier gas used, the temperature of the frit 54, and the atmospheric pressure of the GC environment. The valve V2 controls the pressure across the frit 54.

No flow calculators are present in the split vent branch 40. However, the split vent branch 40 has a valve V3. Instead of performing a flow calculation for the split vent branch 40, the GC controller 35 closes valve V3, setting the flow through that branch to zero (flow$_{split\_vent}$=0). Therefore, the only flow that remains to be determined in equation (2) is flow$_{column}$, which is calculated using previously described methods that are well-known to one of ordinary skill in the art.

Figure 5:
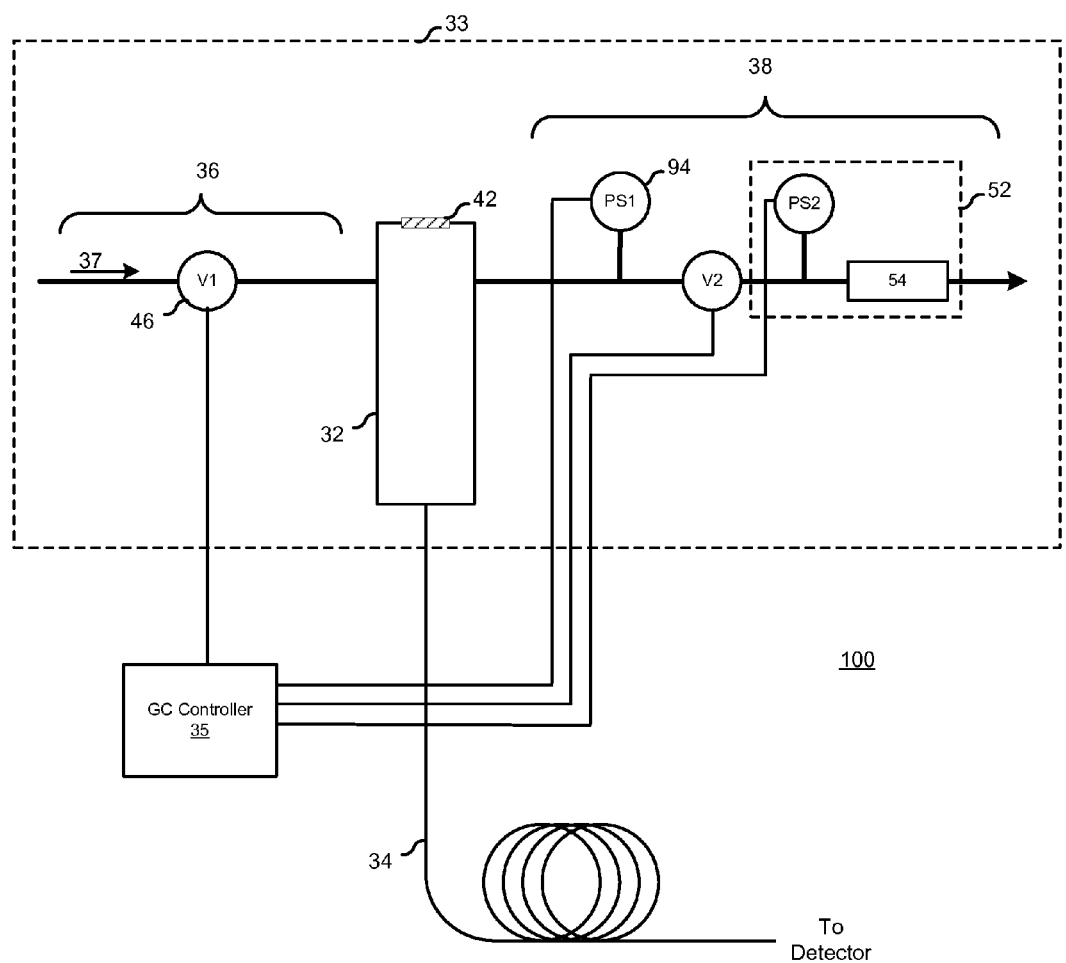
FIG. 5 shows a GC without a split vent branch.

FIG. 5 shows a portion of a GC 100 for performing a flow disruption test according to one embodiment. GC 100 includes a GC inlet 33 that leads to a column 34, and a GC controller 35 for controlling the GC 100. This GC inlet 33 lacks a split vent branch 40 and a flow sensor FS in the input branch 36, and is sometimes referred to as an "on-column" or "cool on-column" inlet. Since the GC 100 is missing a flow sensor in the input branch 36, it is not possible to calculate the total input flow (flow$_{input}$) into the inlet body 32 as required by equation (2). Even so, it is still possible to check for leaks in this GC 100.

The carrier inlet valve V1 is initially left open, to allow carrier gas 37 through to the inlet body 32 and to establish an initial pressure in the inlet body 32. This initial pressure is measured by pressure sensor PS1. Then, the carrier inlet valve V1 is closed. Even in the absence of any leaks, the pressure in the inlet body 32 as measured by the pressure sensor PS1 will drop due to the continuing output flows from the column 34 and the septum purge branch 38. In one embodiment, the septum purge valve V2 is closed both before and after closing the valve V1, so that the only output flow is through the column 34.

The drop in pressure over time is a function of the total flow out of the inlet body 32. Therefore, by monitoring the rate of the pressure drop, the output flow of the GC inlet can be determined. If the rate of pressure drop exceeds a target drop rate, a leak exists that increases the rate of pressure drop beyond what is expected for the GC 100. When this occurs, the GC controller 35 issues a warning that a leak is present somewhere within the GC inlet 33. Similarly, if the rate of pressure drop is slower than a target drop rate, a clog exists within the GC inlet 33 that decreases the rate of pressure drop below what is expected for the GC 100. This calculation may also be performed as a safety feature, since a broken column 34 will also generate a pressure drop rate greater than the target drop rate. The proper target drop rate to use will vary depending on the particular application of the GC 100 and the requirements of the user. The user may calibrate the GC 100 when it is functioning normally to determine an appropriate value for the target drop rate and program that value into the GC controller 35. This method of checking for flow disruptions can be initiated as needed by the user and run by the GC controller 35 as a routine. Or, the GC controller 35 can be programmed to run this test automatically at regular intervals (e.g. after every run, or every day, etc.) or pre-programmed intervals to maintain the GC in working condition.

Figure 6:
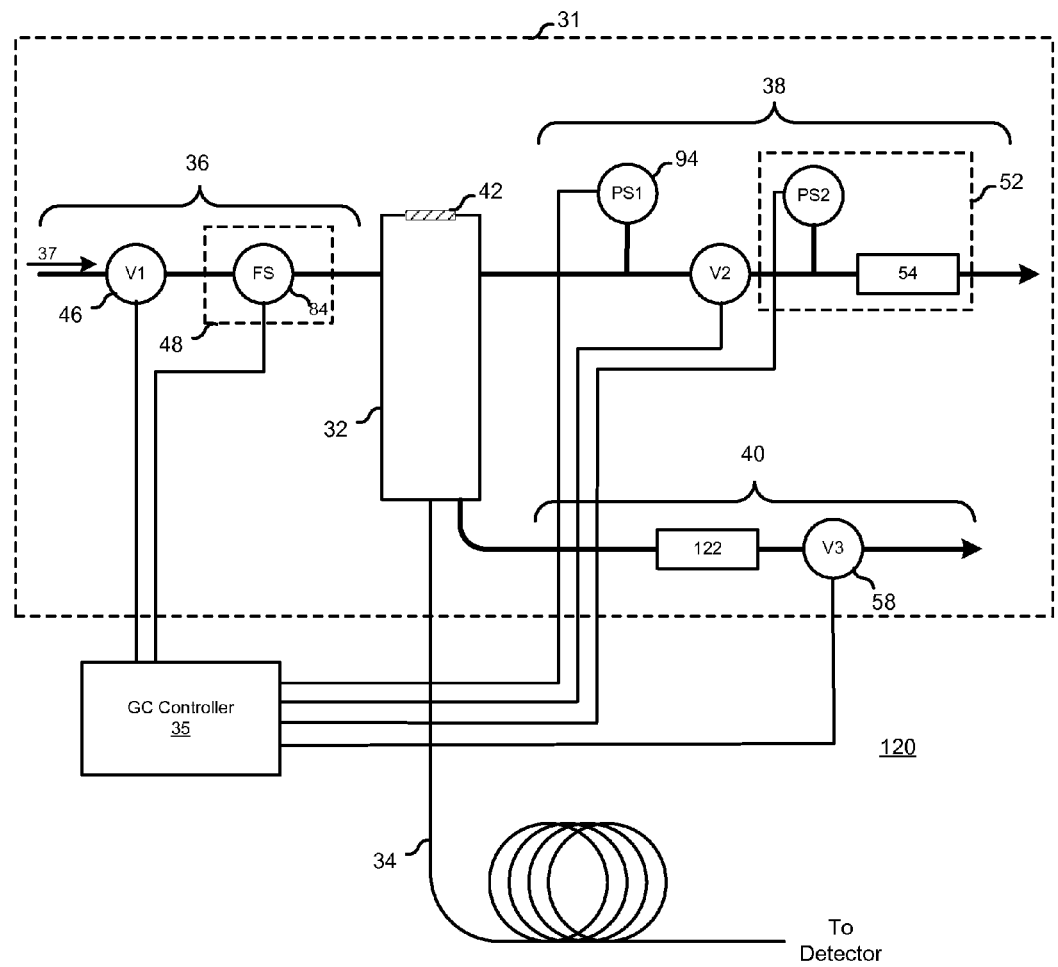
FIG. 6 shows a GC including a split trap in the split vent branch.

FIG. 6 shows a portion of a GC 120 according to one embodiment. GC 120 includes a GC inlet 31 that leads to a column 34, and a GC controller 35 for controlling the GC 120. The GC inlet 31 includes a split trap 122 in the split vent branch 40. In many GCs, a split trap 122 is inserted between the inlet body 32 and the valve V3 to protect the valve V3 from contamination by solvents and materials in the injected sample 45. Normally, V3 functions as a back pressure regulator in the GC: the wider it opens, the lower the pressure in the inlet body 32. However, the split trap 122 may become clogged and prevent the pressure in the inlet body 32 from being lowered, no matter how wide V3 is opened. This may create too large a back pressure to allow an analysis to proceed. A procedure similar to those used to detect a leak in the GCs described above may be used to test whether the split trap 122 is clogged.

First, the split valve V3 is fully opened. With the split valve V3 open, most of the flow (less the flow through the column 34 and septum purge branch 38) goes through the split vent branch 40. The back pressure on the split trap 122 is the current pressure in the inlet body 32, as measured by pressure sensor PS1. If the pressure measured by PS1 is higher than a target inlet pressure, then the split trap 122 is clogged and may need to be cleaned or replaced. Again, the target inlet pressure will vary depending on the particular application of the GC 120 and the requirements of the user. The user may calibrate the GC 120 when it is functioning normally to determine an appropriate value for the target inlet pressure and program that value into the GC controller 35. This method of checking for a clogged split trap can be initiated as needed by the user and run by the GC controller 35 as a routine. Or, the GC controller 35 can be programmed to run this test automatically at regular intervals (e.g. after every run, or every day, etc.) or pre-programmed intervals to maintain the GC in working condition.

Although the present invention has been described in detail with reference to particular embodiments, persons possessing ordinary skill in the art to which this invention pertains will appreciate that various modifications and enhancements may be made without departing from the spirit and scope of the claims that follow.

What is claimed is:

1. A method, comprising:
   controlling an input flow of a gas entering a chamber of a gas chromatograph (GC) inlet;
   controlling an output flow of gas leaving the chamber;
   determining the input flow of the gas entering the chamber;
   determining the output flow of the gas leaving the chamber;
   comparing the input flow and the output flow; and
   detecting a flow disruption based on a difference between the input flow and the output flow.

2. A method as in claim 1, wherein determining the output flow of the gas leaving the chamber further includes:
  determining an output path flow for each output path from the chamber; and
  adding together all output path flows.

3. A method as in claim 2, wherein determining the output path flow for each output path further includes:
  locating a valve within at least one output path from the chamber; and
  closing the valve to set the output path flow for the at least one output path to zero.

4. A method as in claim 3, wherein the at least one output path is a septum purge of the GC inlet.

5. A method as in claim 3, wherein the at least one output path is a split vent of the GC inlet.

6. A method as in claim 1, further comprising:
  measuring a pressure for the chamber, the chamber having an output path for the output flow of gas;
  comparing the measured pressure to a target pressure; and
  detecting a clog in the output path when the chamber pressure exceeds the target pressure.

7. A method as in claim 6, wherein the output path is a split vent including a split trap.

8. A method as in claim 1, further comprising:
  programming a GC controller to perform the steps of;
    (a) controlling the input flow of gas entering the chamber of the GC inlet;
    (b) controlling the output flow of gas leaving the chamber; and
    (c) detecting a flow disruption in the GC inlet based on a deviation of at least one of the input and output flows from the target value,
    at a time in the future.

9. A method comprising:
  establishing a pressure in a chamber of a gas chromatograph (GC) inlet from an input flow of gas;
  stopping the input flow of gas while continuing an output flow of gas;
  measuring a drop rate in the pressure of the chamber;
  comparing the measured drop rate to a target drop rate; and
  detecting a flow disruption in the GC inlet when the measured drop rate deviates from the target drop rate.

10. A method as in claim 9, wherein the chamber has more than one output path for the exit flow of gas, at least one of the output paths including a valve.

11. A method as in claim 10, further comprising:
  closing the valve in at least one output path of the chamber prior to stopping the input flow.

12. A method as in claim 1, wherein:
  controlling the output flow of gas comprises flowing the output flow only though a column connected to the chamber;
  determining the output flow comprises calculating a column flow for the column;
  comparing the input flow to the output flow comprises comparing a measured input flow to the calculated column flow; and
  detecting a flow disruption comprises detecting a flow disruption in the column when the measured input flow deviates from the calculated column flow.

13. A method as in claim 12, further comprising:
  detecting a clog in the column when the measured input flow is lower than the calculated column flow.

14. A gas chromatograph, comprising:
  an inlet including a chamber having an input path for an input flow of gas and a plurality of output paths, each output path corresponding to an output path flow; and
  a controller capable of controlling the input flow and output path flows and detecting a flow disruption based on a deviation of at least one of the input and output path flows from a target value,
  wherein the controller is capable of adding together all output path flows into a total output flow, and detecting a flow disruption when the input flow substantially deviates from the total output flow.

15. A gas chromatograph as in claim 14, further comprising:
  an output valve in at least one of the output paths, wherein the controller is capable of closing the output valve to set the output path flow for the at least one output path to zero.

16. A gas chromatograph as in claim 14, further comprising:
  an input valve that controls the input flow in the input path, the input valve in electronic communication with the controller;
  a pressure sensor that measures pressure in the chamber and electronically communicates a measured chamber pressure to the controller; and
  memory for storing a target drop rate, wherein the controller is capable of closing the input valve and detecting a flow disruption in the inlet when the measured chamber pressure drops at a rate that deviates from the target drop rate.

17. A gas chromatograph as in claim 14, wherein at least one of the output paths is a split vent including a split trap, further comprising:
  a pressure sensor that measures pressure in the chamber and electronically communicates a measured chamber pressure to the controller; and
  memory for storing a target pressure, wherein the controller is capable of detecting a clog in the split vent when the measured chamber pressure exceeds the target pressure.

18. A gas chromatograph as in claim 14, further comprising:
  an input flow sensor that measures the input flow and electronically communicates a measured input flow to the controller;
  wherein the plurality of output paths includes a column connected to the chamber, the column having a column flow calculated by the controller, and the controller is capable of detecting a flow disruption in the column when the measured input flow deviates from the column flow.

* * * * *

UNITED STATES PATENT AND TRADEMARK OFFICE
CERTIFICATE OF CORRECTION

PATENT NO. : 7,559,227 B2  Page 1 of 1
APPLICATION NO. : 11/611771
DATED : July 14, 2009
INVENTOR(S) : Michael Q. Thompson It is certified that error appears in the above-identified patent and that said Letters Patent is hereby corrected as shown below:

In column 7, line 25, in Claim 8, delete "of;" and insert -- of: --, therefor.

In column 7, line 34, in Claim 9, after "method" insert -- , --.

In column 7, line 51, in Claim 12, delete "though" and insert -- through --, therefor.

In column 8, lines 1-2, in Claim 12, delete "when the measured input flow deviates from the calculated column flow." and insert the same after "column" on Col. 7, Claim 12, Line 59 as a continuation of the same line.

Signed and Sealed this

Third Day of November, 2009

David J. Kappos
*Director of the United States Patent and Trademark Office*